United States Patent [19]

Story et al.

[11] Patent Number: 4,944,949

[45] Date of Patent: Jul. 31, 1990

[54] PHARMACEUTICAL DELIVERY SYSTEMS

[75] Inventors: Michael J. Story, Threapwood; Michael J. Flynn, Surrey, both of England

[73] Assignee: T.I.L. Medical Ltd., Middlesex, England

[21] Appl. No.: 134,243

[22] Filed: Dec. 17, 1987

[30] Foreign Application Priority Data

Dec. 18, 1986 [GB] United Kingdom ................ 8630273

[51] Int. Cl.$^5$ ............................................... A61K 9/66
[52] U.S. Cl. .................................... 424/451; 424/455; 424/456; 514/825; 514/937; 514/941
[58] Field of Search ................ 424/450, 451, 455, 456; 514/825, 937, 941

[56] References Cited

U.S. PATENT DOCUMENTS

| | | | |
|---|---|---|---|
| 3,887,700 | 6/1975 | Boncey et al. | 424/44 |
| 4,182,330 | 1/1980 | Michaels | 128/260 |
| 4,344,934 | 8/1982 | Martin et al. | 424/80 |
| 4,690,823 | 9/1987 | Lohner et al. | 424/456 |

FOREIGN PATENT DOCUMENTS

| | | |
|---|---|---|
| 1601613 | 11/1981 | United Kingdom . |
| 0102324 | 7/1983 | European Pat. Off. . |
| 0101294 | 2/1984 | European Pat. Off. . |
| 0178436 | 4/1986 | European Pat. Off. . |
| 0179583 | 4/1986 | European Pat. Off. . |
| 0223369 | 5/1987 | European Pat. Off. . |
| 3315805 | 11/1984 | Fed. Rep. of Germany . |
| 9010524 | 1/1984 | Japan . |
| 148718 | 8/1984 | Japan . |
| 8602264 | 4/1986 | PCT Int'l Appl. . |
| 8603675 | 7/1986 | PCT Int'l Appl. . |

OTHER PUBLICATIONS

Schott et al., The Role of Surfactants in the Release of Very Slightly Soluble Drugs from Tablets, 1982, 71 J. Pharm. Sci., 1038.
Kim and Choe, Effect of Surfactants on the Solubility Properties of Indomethacin, 1984, 28 Yakhak Hoeji, 161.
DT 2802-114 Chemical Abstracts.
Chemical Abstracts DT 2902-672.
Chemical Abstracts 104:193025j.
Chemical Abstracts 104:135951x.
Chemical Abstracts 104:10512y.
Chemical Abstracts 103:183432c.
Chemical Abstracts 101:975552.
Chemical Abstracts 101:12070q.
Chemical Abstracts 98:40512y.
Chemical Abstracts 97:188287d.
Chemical Abstracts 97:12252z.
Chemical Abstracts 95:103216r.
Chemical Abstracts 47718r.
Chemical Abstracts 90:127464t.
Chemical Abstracts 94:127260f.
Chemical Abstracts 94:52772p.
Miyazaki et al., "Micellar Interaction of Indomethacin and Phenylbutazone with Bile Salts", *Int. J. Parm* 8, (1981), 303–310.
Paradies, H. "Structure of Phenylbutazone and Mofebutazone in the Crystalline State and in Solution", *J. Pharm Sci.*, 76(12), 920–929.
Maher et al., "Structural Changes in Membranes Produced by Building of Small Amphipathic Molecules", *Biochem.*, 1984, (23), 232–240.
Chemical Abstracts 85:166564s; 104:155882d; 104:155883e; 108:192665p; 106:6723s; 94:52771n.

*Primary Examiner*—Olik Chaudhuri
*Assistant Examiner*—Andrew Griffis
*Attorney, Agent, or Firm*—Fish & Richardson

[57] ABSTRACT

Non-steroidal anti-inflammatory drugs (NSAIDs) including diclofenac, flufenamic acid, flurbiprofen, ibuprofen, indomethacin, ketoprofen, naproxen, phenylbutazone, piroxicam and sulindac are administered in micelles to alleviate their adverse effects on the gastrointestinal tract. The drugs are formulated with surfactants such as polyethoxylated nonionics to give micelle-forming compositions.

15 Claims, No Drawings

PHARMACEUTICAL DELIVERY SYSTEMS

This invention relates to pharmaceutical compositions for use in the treatment of inflammatory arthropathy.

Inflammatory arthropathy is the general name for a collection of debilitating and painful diseases which are extremely common in many countries of the world. Their classification is somewhat difficult, but inflammatory arthropathy or rheumatic disease seem to be the most common generic terms. In this specification, the term "inflammatory arthropathy" is used as the preferred generic term, but is to be understood to include forms of the disease known to some practitioners as rheumatic disease.

Of the various forms of inflammatory arthropathy, osteoarthrosis (or osteoarthritis) on the one hand and rheumatoid arthritis on the other hand are the commonest. Some workers in the field prefer the term osteoarthrosis to the term osteoarthritis, although it has been suggested that there is a place for both words. It is has been suggested that osteoarthrosis is the most sensible way of labelling the presence of simple degenerative joint disease but osteoarthritis separates the acute episodes of an inflammatory nature which occur in degenerative joint disease.

Osteoarthrosis usually has an insidious onset of pain, stiffness and a reduced range of movement. It commonly effects one or only a small number of joints. Intermittent swelling due to an effusion or an inflammatory episode in the affected joint may appear and, later in the disease, a permanent increase in size or change of shape may result from bony enlargement. Joint laxity develops with locking and grating.

It is often the joints which have been used the most or previously effected by trauma or inflammatory processes that suffer greatest damage. Thus, the weight-bearing joints of the hips and knees, the lumbar spine and the thumb bases (first capometacarpal joints) are common victims of the disease. The latter are particularly effected in those who have been manual workers or even keen knitters.

The essential features of rheumatoid arthritis are pain and swelling of several joints with morning stiffness continuing for at least a few weeks. Rheumatoid arthritis tends to affect the peripheral small joints symmetrically. Whereas the joints in osteoarthrosis may be described as dry, in rheumatoid arthritis they are "juicy", often swollen, hot, tender and red. There may also be accompanying systemic symptoms of a general malaise, weight loss, anorexia, mild fever and, on investigation, the finding of a normochromic (or hypochromic) normocytic anaemia.

Other common causes of inflammatory arthropathy include viral arthritis, ankylosing spondylitis, psoriatic arthropathy, Reiter's disease, gouty arthritis, septic arthritis (suppurative arthritis), erythema nodosum and Henoch-Schoenlein purpura. The most important in the present context are ankylosing spondylitis and gouty arthritis.

Ankylosing spondylitis is characterised by the gradual onset of low-back pain (sometimes bilateral buttock pain) with morning stiffness. Peripheral joints may become effected. There is a reduced range of spinal movement and chest expansion. Rigidity of the spine follows, often in a cranial direction (first lumbar, then dorsal then cervical) with a characteristic clinical picture of high dorsal kyphosis, obliteration of lumbar lordosis and flattening of the chest.

Gouty arthritis is due to the deposition of monosodium urate monohydrate crystals in the joint. Gouty arthritis is a very common disease: it is estimated that there are over 300,000 sufferers in the United Kingdom alone. The popularly held belief that gout is largely due to an over indulgence of port and pheasant is mainly fallacious, although provocative factors may often be related to its onset. Examples include trauma, surgery, unusual physical exercise, severe illness, dietary excess, alcohol and drugs. Any joint may be affected, and the onset may be polyarticular. Affected joints are painful, red, hot, swollen and exquisitely tender.

The treatment of inflammatory arthropathy has naturally received a fairly large amount of attention from pharmacologists and pharmaceutical manufacturers.

A first class of drugs that have been used in the treatment of inflammatory arthropathy are steroids. Cortisol and its synthetic analogues have the capacity to prevent or supress the development of the local heat, redness, swelling and tenderness by which inflammation is recognised. At the microscopic level they inhibit not only the early phenomena of the inflammatory process (oedema, fibrin deposition, capillary dilation, migration of leukocytes into the inflamed areas and phagocytic activity) but also the later manifestations (capillary proliferation, fibroblast proliferation, deposition of collagen and, still later, cicatrization).

In clinical terms, the administration of such corticosteroids for their anti-inflammatory effects is palliative therapy. The underlying cause of the disease remains; the inflammatory manifestations are merely suppressed. Nevertheless, they are effective in affording symptomatic relief, but prolonged administration of corticosteroids may be a very high price to pay for such relief: the adrenal cortex may become atrophied, thereby limiting the body's own ability to survive and adapt in a constantly changing environment. The adrenal cortex is the organ of homeostasis: in the absence of the adrenal cortex, survival is possible, but only under the most rigidly prescribed conditions. In more general terms, it has long been recognised that corticosteroids are powerful drugs with slow cumulative toxic effects on many tissues, which may not be apparent until made manifest by a catastrophe.

In the treatment of inflammatory arthropathy, the focus of attention shifted from steroids to a structurally unrelated group of compounds known as slow acting anti-rheumatic drugs (SAARDs). SAARDs have empirically been categorised into three groups. Group I, including drugs of proven value which are widely used, encompasses azathioprine, chloroquine, D-penicillamine and gold salts. Group II relating to clinically active drugs under continuing investigation, includes cyclophosphamide, dapsone, levamisole, methotrexate, sulphasalazine, thiols and thymopoietin. The group III SAARDs are those of less practical or unproven treatment; this group includes methylprednisolone pulsing.

The range of SAARDs is considerable, as has been seen above, and despite much experimental work their modes of action are largely unknown. Logistical and toxicity factors prevent the use of SAARDs in all patients.

A third category of drugs for use in the treatment of inflammatory arthropathy consists of the non-steroidal anti-inflammatory drugs (NSAIDs). Aspirin is the prototype NSAID, and for this reason this group of drugs is also known as the "aspirin-like" drugs. This secondary nomenclature gives a key to a functional similarity of NSAIDs in the absence of any overall chemical similarity: they all appear to owe their anti-inflammatory action, at least in part, to the inhibition of prostaglandin synthesis. According to Goodman and Gilman in "The Pharmacological Basis of Therapeutics" MacMillan 7th Edition 1985, it has been established in recent years that:
1. All mammalian cell types studied (with the exception of the erythrocyte) have microsomal enzymes for the synthesis of prostaglandins;
2. Prostaglandins are always released when cells are damaged and have been detected in increased concentrations in inflammatory exudates all available evidence indicates that cells do not store prostaglandins, and their release thus depends on biosynthesis de novo;
3. All aspirin-like drugs inhibit the biosynthesis and release of prostaglandins in all cells tested; and
4. With the exception of the anti-inflammatory glycocorticoids, other classes of drugs generally do not affect the biosynthesis of prostaglandins.

NSAIDs (or aspirin-like drugs—the two terms are used interchangeably in this specification) can be categorised conveniently into six structural groups. First, there are the salicylic acids and esters including aspirin, benorylate, aloxiprin, salsalate and choline magnesium trisalicylate.

Secondly, there are the propionic acid derivatives, including ibuprofen, naproxen, flurbiprofen, ketoprofen, fenoprofen, fenbufen, benoxaprofen and suprofen.

Thirdly, there is the class of oxicams, including piroxicam.

Fourthly, acetic acid derivatives can be split into two subclasses. Phenylacetic acids include diclofenac and fenclofenac; carbo- and heterocyclic acetic acids include indoles such as indomethacin and sulindac and pyrroles such as tolmetin.

Fifthly, there are the pyrazolones which include oxyphenbutazone, phenylbutazone, feprazone and azapropazone.

Sixthly, the fenamic acid derivatives include flufenamic acid and mefenamic acid.

NSAIDs have emerged as the drugs of choice in the treatment of inflammatory arthropathy. This is possibly more due to the disadvantages associated with other classes of drugs than in anything else. As indicated previously, the inflammatory diseases of the joints cause an extremely high level of discomfort and in many instances the results are crippling. The requirement for treatment is unquestioned and the treatment is in many cases chronic, that is to say it is continuous as the diseases are generally incurable. Unfortunately, the common element in the therapeutic properties of the common NSAIDs is also the principle cause of side effects. As has been mentioned, the salicylates and other NSAIDs are thought to be effective in inflammatory joint disease, and their effectiveness is thought to be partly mediated through prostaglandin inhibition. Prostaglandins have been shown to have a protective effect on the gastrointestinal mucosa and, therefore, drugs which inhibit their activity are likely to cause gastrointestinal intolerance. Drugs with a potent inhibitory action on prostaglandin synthetase are marketed as having a potent anti-inflammatory action but have been shown to cause more faecal blood loss than those with weak antiprostaglandin activity. Aspirin, for example, causes as much as an 8- to 10-fold increase in faecal blood loss and indomethacin a nearly 3-fold loss, compared with controls. However, when oral prostaglandin $E_2$ ($PGE_2$) at doses of 1 mg three or four times daily is given with indomethacin or aspirin, the blood loss is reduced to control levels without reducing the effectiveness of the drugs.

Protection of the stomach from the drug has in some circumstances been shown to be effectively achieved by the use of enteric coating, as demonstrated by enteric coated aspirin preparations. However, the use of conventional enteric coating means that the drug is released in the neutral or slightly alkaline environment of the small or large intestine, which consequently experiences a considerably heightened local concentration from direct contact by the drug. Intestinal ulceration can occur with chronic administration of NSAIDs.

There is therefore a need for an improved and safer form of administration of NSAIDs to give protection both in the stomach and in the intestine. In addition, it would be advantageous to be able to provide a means of enhancing the absorption of the NSAIDs, which tend to be poorly water soluble, as well as providing an improved concentration of the drug at the cellular level at the site of its action. It is known that drugs with a low water solubility have a slow and variable dissolution pattern which can lead to reduced and erratic bioavailabilty. In short, what has been needed for some time is a delivery system for NSAIDs which protects the gastrointestinal tract from the drug, and which provides a means of alleviating the difficulties associated with very poor water solubility.

The present invention is based on the discovery that the use of micelles enables a particularly appropriate form of administration of NSAIDs to be achieved.

According to a first aspect of the present invention, there are provided micelles containing a non-steroidal anti-inflammatory drug.

Although NSAIDs themselves tend not to form micelles, amphipathic compounds, known more familiarly as surfactants, can form micelles. Surfactants have two distinct regions in their chemical structure, termed hydrophilic (water-liking) and hydrophobic (water-hating) regions. Micelles are aggregates in which the surfactant molecules are generally arranged in a spheroidal structure with the hydrophobic region at the core shielded, in a aqueous solution, from the water by a mantle of outer hydrophilic regions. According to a second aspect of the invention, therefore, there is provided a pharmaceutical composition comprising a non-steroidal anti-inflammatory drug and a surfactant, the composition being capable of forming micelles containing the non-steroidal anti-inflammatory drug when administered orally. It will generally be the case that the drug will be dissolved in the surfactant. In its simplest form, the pharmaceutical composition can be a solution of the drug in a surfactant, although other components may be present in the system if desired or necessary.

In a third aspect, the invention provides a process for the preparation of an anti-inflammatory composition capable of forming non-steroidal anti-inflammatory drug-containing micelles on oral adminstration to a human or non-human animal, the process comprising admixing a non-steroidal anti-inflammatory drug with a surfactant. The process may involve dissolving the drug in the surfactant.

According to a fourth aspect, the invention provides the use of a non-steroidal anti-inflammatory drug and a surfactant in the preparation of a composition for administering the drug in micellar form. Insofar as the law allows, the invention also relates to a method for the treatment or prophylaxis of inflammatory arthropathy, the method comprising the administration of micelles containing a non-steroidal anti-inflammatory drug.

Micelles are to be contrasted in terms of their structure with vesicles and with liposomes. Vesicles are aggregates of amphipathic molecules arranged in a bilayer. Typically, a vesicle will have a hydrophilic interior and a hydrophilic exterior: hydrophilic regions of an internal layer of the molecules will be directed inwardly, and hydrophilic regions of an outer layer of the molecule will be directed outwardly. Hydrophobic regions of the two layers will be directed towards one another within the molecular wall of the vesicle.

Liposomes are nothing more than multilamellar vesicles, as is revealed by the fact that liposomes disintegrate to vesicles upon ultrasonication.

Surfactants can be variously classified, and often by reference to the nature of the hydrophilic region, which can be anionic, cationic, zwitterionic or nonionic. In the present invention, nonionic surfactants are preferred. A particularly preferred subcategory of nonionic surfactants are polyoxyethylated surfactants, including polyoxyethylated glycol monoethers, polyoxyethylated fatty acids, polyoxyethylated sorbitan fatty esters, and polyoxyethylated castor oils. However, other nonionic surfactants are also particularly appropriate, including sorbitan fatty acid esters, poloxamers, polyethylene glycol fatty acid esters and polyethoxylated glyceryl fatty acid esters.

Whatever the precise chemical structure of the surfactant or surfactants used, it is generally preferred to use one or more of those that have been already cleared for human ingestion. Therefore, surfactants with a low toxicity are preferred. For example, surfactants having an $LD_{50}$ exceeding 10 g/kg and preferably 15 g/kg, are generally suitable. The absence of other side effects is of course also appropriate. Although surfactants which have already been approved for human ingestion are naturally preferred, the use of other surfactants is not ruled out, not least because they may in time come to be approved for human ingestion.

The availability of nonionic surfactants is not perceived to be a cause of difficulty. For example, the following surfactants are known to be available.

Polyoxyethylene Alkylphenols

| POE(n) octylphenol | n = 1–70 | Triton X series (Rohm & Haas) Igepal CA series (GAF, USA) Antarox CA series (GAF, UK) |
| POE(n) nonylphenol | n = 1.5–100 | Triton N series (Rhom & Haas) Igepal CO series (GAF, USA) Antarox CO series (GAF, UK) |

None of the polyosyethylene alkylphenols are as yet approved for human ingestion.

Polyosyethylated Glycol Monoethers

| POE(n) lauryl ether | n = 4,23 | Volpo L series (Croda) Brij 30 series (Atlas/ICI Specialties, UK) |
| POE(n) cetyl ether | n = 2,10,20 | Brij 50 series (Atlas/ICI) |
| POE(n) stearyl ether | n = 2,10,20 | Brij 70 and 700 series (Atlas/ICI) |
| POE(n) oleyl ether | n = 2–20 | Volpo N series (Croda) |

-continued

| POE(n) ceto/stearyl ether | n = 3–20 | Brij 90 series (Atlas/ICI) Volpo CS series (Croda) |

None of these have been approved for internal use, although Cetomacrogol 1000 (Brij 58, Volpo CS20) has been extensively used in topical applications.

Polyoxyethylated Glyceryl Fatty Acid Esters

POE(n) glyceryl monolaurate n=15,40 Glycerox L series (Croda)

These products have not been cleared for internal ingestion.

Polyoxyethylated Fatty Acids

| POE(n) monolaurate | n = 4–100 | Crodet L series (Croda) |
| POE(n) monooleate | n = 4–100 | Crodet O series (Croda) |
| POE(n) monostearate | n = 4–100 | Crodet S series (Croda) Myrj series (Atlas/ICI) |

POE(8) monostearate and POE(40) monostearate appear to be approved for internal ingestion in the UK and EEC, and the latter is also approved by the FDA in the US. The other POE(n) monostearates appear valid contenders for approval, with the POE(n) monooleates and monolaurates also being likely candidates.

Sorbitan Fatty Acid Esters

| Sorbitan monolaurate | Crill 1 (Croda) Span 20 (Atlas/ICI) |
| Sorbitan monopalmitate | Crill 2 (Croda) Span 40 (Atlas/ICI) |
| Sorbitan monostearate | Crill 3 (Croda) Span 60 (Atlas/ICI) |
| Sorbitan tristearate | Crill 35 (Croda) Span 65 (Atlas/ICI) |
| Sorbitan monooleate | Crill 4 (Croda) Span 80 (Atlas/ICI) |
| Sorbitan sesquioleate | Crill 43 (Croda) |
| Sorbitan trioleate | Crill 45 (Croda) Span 85 (Atlas/ICI) |
| Sorbitan monoisostearate | Crill 6 (Croda) |

The surfactants in this group have good approval rating in the UK, EEC and US, but not complete approval.

Polyoxyethylated Sorbitan Fatty Acid Esters

| POE(20) sorbitan monolaurate | Crillet 1 (Croda) Tween 20 (Atlas/ICI) |
| POE(4) sorbitan monolaurate | Crillet 11 (Croda) Tween 21 (Atlas/ICI) |
| POE(20) sorbitan monopalmitate | Crillet 2 (Croda) Tween 40 (Atlas/ICI) |
| POE(20) sorbitan monostearate | Crillet 3 (Croda) Tween 60 (Atlas/ICI) |
| POE(4) sorbitan monostearate | Crillet 31 (Croda) Tween 61 (Atlas/ICI) |
| POE(20) sorbitan tristearate | Crillet 35 (Croda) Tween 65 (Atlas/ICI) |
| POE(20) sorbitan monooleate | Crillet 4 (Croda) Tween 80 (Atlas/ICI) |
| POE(5) sorbitan monooleate | Crillet 41 (Croda) Tween 81 (Atlas/ICI) |
| POE(20) sorbitan trioleate | Crillet 45 (Croda) Tween 85 (Atlas/ICI) |
| POE(20) sorbitan monoisostearate | Crillet 6 (Croda) |

These surfactants have a similar approval profile to the Sorbitan Fatty Acid Esters, above.

Polyoxyethylated Castor Oils

| | | |
|---|---|---|
| POE(n) castor oil | n = 10–100 | Etocas Series (Croda) |
| | | Cremophor EL (BASF) |
| POE(n) hydrogenated castor oil | n = 10–100 | Croduret series (Croda) |
| | | Cremophor RH40 (BASF) |

Cremophor EL and Cremophor RH40 are well established as orally ingestable surfactants. It is envisaged that there would be no problems in registers the Etocas or Corduret series provided BP Castor Oil was used in manufacture of the surfactant.

Poloxamers

| | |
|---|---|
| POE(n)-POP(m) | Synperonic PE series(ICI Petrochem & Plastics Div) |
| | Pluronic series (Wyandotte Chem. Corp. USA) |

Some of these have been used in orally ingested pharmaceuticals. They are of low toxicity.

Polyethylene Glycol Fatty Acid Esters

| | | |
|---|---|---|
| PEG(400) distearate | | Cithrol 4DS (Croda) |
| PEG(400) monolaurate | | Cithrol 4ML (Croda) |
| PEG(n) monooleate | n = 200,300, 400 | Cithrol MO series (Croda) |
| PEG(400) dioleate | | Cithrol 4DO (Croda) |
| PEG(n) monostearate | n = 400,600 1000 | Cithrol MS series (Croda) |

There are no toxicology data readily available for these surfactants.

One factor affecting the choice of surfactant or surfactants to be used is the hydrophilic-lipophilic balance (HLB), which gives a numerical indication of the relative affinity of the surfactant for aqueous and non aqueous systems. Surfactants having an HLB of about 10 or above, particularly about 12 or above, are preferred. However, there may be cases where a mixture of two or more surfactants provides an improved degree of solubilization over either surfactant used alone.

In addition to the HLB, the nature of the hydrophobic chain may be taken into account. For example, increasing the degree of unsaturation may improve the potential for solubilization, as may increasing the chain length and/or having branches. Further a reduction in the molecular weight may give improved solubilization on a weight for weight basis, even at the expense of a slight reduction in the HLB. It has been discovered that it is the provision of the solubilizing interior of the micelles which is important, and this may be related to the formation of a solution of the drug in the surfactant prior to the addition of the aqueous phase.

The physical nature of the surfactants will also be a factor to be taken into consideration when choosing surfactants for a particular formulation. The choice of surfactant will, among other things, depend on the type of formulation. For example, a formulation in the form of a solution may be in the form of a liquid, although a solid surfactant may be used in formulating a solution. Soft gelatin capsules may be formulated using a surfactant in the form of a liquid, a viscous liquid or melted waxy solid. Hard gelatin capsules may be formulated using a liquid, a paste (melted) or a solid (melted) surfactant. There follows below a list of potential nonionic surfactants, together with a description of their physical nature and an indication of their HLB and $LD_{50}$.

| Chemical Identity | | Description | HLB | LD50 g/kg |
|---|---|---|---|---|
| Polyoxyethylated Glycol Monoethers | | | | |
| POE(4) | lauryl ether | Water white liquid | 9.5 | 9 |
| POE(23) | lauryl ether | Off-white soft solid | 17.0 | 9 |
| POE(2) | cetyl ether | White solid | 5.3 | 22 |
| POE(15) | cetostearyl ether | Off-white waxy solid | 14.6 | ? |
| POE(20) | cetostearyl ether | Off-white hard waxy solid | 15.6 | 3.6 |
| POE(15) | oleyl ether | Pale straw paste | 14.2 | ? |
| POE(20) | oleyl ether | Pale straw soft solid | 15.5 | 15.1 |
| POE(2) | stearyl ether | White solid | 4.9 | >25 |
| POE(2) | oleyl ether | Pale yellow liquid | 4.9 | 25 |
| Polyoxyethylated Fatty Acids | | | | |
| POE(4) | monolaurate | Pale straw liquid | 9.3 | ? |
| POE(8) | monolaurate | White soft solid | 12.7 | ? |
| POE(12) | monolaurate | White soft solid | 14.5 | ? |
| POE(24) | monolaurate | White waxy solid | 16.8 | ? |
| POE(40) | monolaurate | White hard solid | 17.9 | ? |
| POE(100) | monolaurate | White hard solid | 19.1 | ? |
| POE(4) | monooleate | Yellow/amber liquid | 7.7 | ? |
| POE(8) | monooleate | Yellow/amber liquid | 10.4 | ? |
| POE(12) | monooleate | Yellow/amber liquid | 13.4 | ? |
| POE(24) | monooleate | Yellow/amber paste/solid | 15.8 | ? |
| POE(40) | monooleate | Yellow soft solid | 17.4 | ? |
| POE(100) | monooleate | Yellow waxy solid | 18.8 | ? |
| POE(4) | monostearate | White soft waxy solid | 7.7 | ? |
| POE(8) | monostearate | White waxy solid | 11.1 | 64 |
| POE(12) | monostearate | White waxy solid | 13.4 | ? |
| POE(20) | monostearate | White waxy solid | 15.0 | 10 |
| POE(24) | monostearate | White waxy solid | 15.8 | ? |
| POE(30) | monostearate | White hard solid | 16.0 | ? |
| POE(40) | monostearate | White hard solid | 16.9 | >30 |
| POE(50) | monostearate | White hard solid | 17.9 | >25 |
| POE(100) | monostearate | White hard solid | 18.8 | 25 |
| Sorbitan Fatty Acid Esters | | | | |
| Sorbitan monolaurate | | Pale yellow viscous | 8.6 | 41 |

-continued

| Chemical Identity | | Description | HLB | LD50 g/kg |
|---|---|---|---|---|
| | | liquid | | |
| Sorbitan monopalmitate | | Pale tan waxy solid | 6.7 | >16 |
| Sorbitan monostearate | | Pale tan waxy solid | 4.7 | 31 |
| Sorbitan tristearate | | Pale tan waxy solid | 2.1 | >16 |
| Sorbitan monooleate | | Amber viscous liquid | 4.3 | >40 |
| Sorbitan sesquioleate | | Amber viscous liquid | 3.7 | ? |
| Sorbitan trioleate | | Amber viscous liquid | 1.8 | >40 |
| Sorbitan monoisostearate | | Yellow viscous liquid | 4.7 | ? |
| Polyoxyethylated Sorbitan Fatty Esters | | | | |
| POE(20) | sorbitan monolaurate | Pale yellow liquid | 16.7 | >39 |
| POE(4) | sorbitan monolaurate | Yellow/amber liquid | 13.3 | >38 |
| POE(20) | sorbitan monopalmitate | Yellow pasty liquid | 15.6 | >38 |
| POE(20) | sorbitan monostearate | Yellow pasty liquid | 14.9 | >38 |
| POE(4) | sorbitan monostearate | Pale yellow waxy solid | 9.6 | >40 |
| POE(20) | sorbitan tristearate | Cream waxy solid | 10.5 | >40 |
| POE(20) | sorbitan monooleate | Yellow/amber liquid | 15.0 | >38 |
| POE(5) | sorbitan monooleate | Yellow/amber liquid | 10.0 | >37 |
| POE(20) | sorbitan trioleate | Yellow/amber liquid | 11.0 | >36 |
| POE(20) | sorbitan monoisostearate | Yellow liquid | 14.9 | ? |
| Polyoxyethylated Castor Oils | | | | |
| POE(10) | castor oil | Pale yellow liquid | 6.3 | ? |
| POE(35) | castor oil | Pale yellow liquid | 12.5 | >10 |
| POE(40) | castor oil | Pale yellow liquid | 13.0 | ? |
| POE(60) | castor oil | Pale yellow soft paste | 14.7 | ? |
| POE(100) | castor oil | Pale yellow waxy solid | 16.5 | ? |
| POE(10) | hydrogenated castor oil | Pale straw liquid | 6.3 | ? |
| POE(30) | hydrogenated castor oil | Pale straw liquid | 11.6 | ? |
| POE(40) | hydrogenated castor oil | White soft paste | 13.0 | ? |
| POE(45) | hydrogenated castor oil | White soft paste | 14 | >16 |
| POE(60) | hydrogenated castor oil | White soft paste | 14.6 | ? |
| POE(100) | hydrogenated castor oil | White waxy solid | 16.4 | ? |
| Poloxamers | | | | |
| POE(22) | - POP (13) (L35) | Liquid | 18.5 | |
| POE(90) | - POP (13) (F38) | Solid | 30.5 | |
| POE(7) | - POP (17) (L42) | Liquid | 8 | |
| POE(20) | - POP (17) (L44) | Liquid | 16 | |
| POE(4) | - POP (23) (L61) | Liquid | 3 | |
| POE(10) | - POP (23) (L62) | Liquid | 7 | |
| POE(27) | - POP (23) (L64) | Liquid | 7 | |
| POE(159) | - POP (23) (F68) | Solid | 15 | |
| POE(47) | - POP (27) (P75) | Paste | 16.5 | |
| POE(6) | - POP (30) (L81) | Liquid | 2 | |
| POE(51) | - POP (30) (P85) | Paste | 16 | |
| POE(119) | - POP (30) (F87) | Solid | 24 | |
| POE(205) | - POP (30) (F88) | Solid | 28 | |
| POE(19) | - POP (37) (L92) | Liquid | 5.5 | |
| POE(41) | - POP (37) (P94) | Paste | 13.5 | |
| POE(8) | - POP (43) (L101) | Liquid | 1 | |
| POE(32) | - POP (43) (P103) | Paste | 9 | |
| POE(296) | - POP (43) (F108) | Solid | 27 | |
| POE(10) | - POP (53) (L121) | Liquid | 0.5 | |
| POE(193) | - POP (53) (F127) | Solid | 22 | |

Various non-steroidal anti-inflammatory drugs in common use today tend to have, as a common property, the property of being poorly soluble in water. The poor solubility does nothing to ameliorate the problems of their administration in conventional delivery systems, and the present invention provides a means of overcoming at least some of the difficulties associated with poor water solubility. Apart from anything else, particles of insoluble drug may tend to lie in folds of the intestinal mucosa, thereby giving rise to local irritancy.

There follows a brief discussion of each of the NSAIDs which are, in accordance with the present invention, particularly appropriate for being delivered in the form of micelles.

Diclofenac is sold as the free acid under the trade mark VOLTAROL by Geigy Pharmaceuticals. It is poorly soluble in water but soluble in some organic solvents. Gastrointestinal disturbances have been reported in about 7% of all cases. In general, it is fairly well absorbed, but more than 99% of the drug has been found to be bound to plasma proteins. The drug has been recommended for use in the treatment of rheumatoid arthritis and other rheumatic disorders at a dose of from 75 to 150 mg per day, depending upon the form of administration and its frequency. Diclofenac has been supplied as enteric coated tablets, slow release tablets, suppositories and in ampoules.

Flufenamic acid is sold under the trade mark MERALEN by Merrell Dow Pharmaceuticals. Its solubility is less than 1 part in 10,000 parts of water, although it is reasonably soluble in various organic solvents. Its most frequent adverse effects are gastrointestinal disturbances. The drug is well absorbed and is extensively bound to plasma proteins. It is prescribed for rheumatic disorders at doses of from 400 to 600 mg per day.

Flurbiprofen is sold under the trade mark FROBEN by the Boots Company plc. It is soluble in 100 to 1,000 parts of water only, but is readily soluble in most organic solvents. Gastrointestinal side effects have been reported in from 23 to 27% of cases. It is readily absorbed, approximately 99% of the drug being bound to plasma proteins It is prescribed for rheumatoid arthritis and other rheumatic disorders and doses from 150 to 200 mg per day in a divided dose. The maximum dosage is stated to be 300 mg per day.

Another Boots Company drug is ibuprofen sold under the trade mark BRUFEN. Other trade marks in the UK for ibuprofen are FENBID and APSIFEN and in the US are RUFEN, ADVIL, MOTRIN and NUPRIN. It is poorly soluble in water: less than 1 part of drug will dissolve in 10,000 parts of water. However, it is fairly soluble in simple organic solvents. The most frequent adverse effects reported are, again, gastrointestinal. The drug is well absorbed and extensively bound to plasma proteins in vivo. It is prescribed for rheumatic arthritis and other musculoskeletal disorders, as well as acute gout. The dosage of the drug is from 600 to 1200 mg daily in divided doses, with 2,400 mg per day being the maximum.

Indomethacin is sold under the trade mark INDOCID by Thomas Morson Pharmaceuticals. It is also sold under the trade mark INBRILON in the UK and INDOCIN in the US. One part of drug is only soluble in more than 10,000 parts of water, but is more soluble in simple organic solvents. The most frequently reported adverse effects are gastrointestinal problems, headache and dizziness. The drug is readily absorbed, with more than 90% being bound to plasma proteins. It is prescibed for rheumatoid arthritis, ankylosing spondylitis, osteoarthritis and other rheumatic disorders, as well as acute gout. The recommended dosage is up to 150 to 200 mg daily in divided doses.

Ketoprofen is sold under the trade mark ORUDIS by May & Baker Limited, who also market controlled release pellets of the drug under the trade mark ORUVAIL. It is also sold in the UK under the trade mark ALRHEUMAT. Its solubility is less than 1 part in 10,000 parts of water, but it is freely soluble in various simple organic solvents. The most frequent side effects are gastrointestinal. The drug is readily absorbed and is extensively bound to plasma proteins. It is prescribed for rheumatoid arthritis and osteoarthritis at doses of from 50 to 100 mg twice daily.

Naproxen is sold under the trade mark NAPROSYN by Syntex Pharmaceuticals Limited. Naproxen sodium is sold as SYNFLEX. The solubility of the free acid is less than 1 part in 10,000 parts water, but the drug is more soluble in simple organic solvents. The most frequent adverse effects reported are gastrointestinal. The drug is readily absorbed with more than 99% being bound to plasma proteins. Naproxen is prescribed for rheumatoid arthritis and other rheumatic or musculoskeletal disorders, dysmenorrhoea and acute gout. Its recommended dosage is from 500 to 1,000 mg daily in divided doses, with from 250 to 375 mg twice daily being preferred.

Phenylbutazone has been sold in the UK under the trade mark BUTAZOLIDIN by Geigy Pharmaceuticals; it is still available in the United States. Its solubility is less than 1 part in 10,000 parts of water, but it is more in common organic solvents. Its most adverse effects are nausea, vomiting and epigastric distress. It is readily absorbed, with 98% of the drug being bound to plasma proteins. It is generally only prescribed for the treatment of rheumatic disorders where other drugs have failed. The initial recommended dosage ranges from 400 to 600 mg per day, but this should decrease to a maintenance dosage of from 200 to 300 mg per day. In both cases, the dosages should be divided through the day. The maximum daily dosage is 800 mg.

Piroxicam is marketed in the UK under the trade mark FELDENE by Pfizer Limited. It is known to be poorly soluble in water but soluble in some organic solvents. There is a high incidence of severe gastrointestinal side effects. The drug is well absorbed with 99% being bound to plasma proteins. It is prescribed for rheumatoid arthritis and other rheumatic disorders, as well as acute gout at dosages of from 10 to 30 mg per day, with 20 mg per day being preferred.

Sulindac is sold in the UK under the trade mark CLINORIL by Merck, Sharp & Dohme Limited. Its solubility is less than 1 part in 10,000 parts water, although it is slightly soluble in simple organic solvents. The most frequent side effects claimed of are gastrointestinal, headache and dizziness. It is incompletely absorbed from the gastrointestinal tract. It is prescribed for rheumatic and other musculoskeletal disorders at dosages of from 400 to 600 mg per day.

Specific paediatric preparations include:
Ibuprofen 200 ml × 100 mg/5 ml syrup;
Indomethacin 200 ml × 25 mg/5 ml suspension (UK, but nor recommended in US for children under 14 years); and
Naproxen 500 ml × 25 mg/ml suspension.

Ketoprofen appears to be a possible further candidate for paediatric use.

Various surfactants and NSAIDs suitable for use in the present invention have now been described. However, the list is not to be taken as exhaustive. In addition, it should not be assumed that only these two ingredients have to be present as in some cases, including capsules, anti-oxidants will be required to ensure adequate stability. When preparing solutions, for example, for paediatric or geriatric use, additional excipients may be present such as preservatives, sweeteners and flavouring agents.

In certain cases it may be required to formulate an NSAID capsule which has sustained release properties. In such cases it is appropriate to include in the formulation ingredients which slow down the release of the surfactant/NSAID combination from the total capsule mix. Such ingredients will generally be of a waxy nature, but this will not exclude the opportunity of using other techniques such as pellets with controlled release coatings.

The relative proportions of drug and surfactant used will, in the main, depend upon (a) the drug, (b) the surfactant and (c) the intended formulation, be it hard gelatin capsules, liquid solution or whatever. When preparing a micelle-forming drug/surfactant mix for use in capsules, it may be found appropriate to use the drug and surfactants in a weight ratio (drug:surfactant) of from 1:5.7 to 1:50, for example, from 1:6 to 1:20 or 1:25. When preparing solutions for, for example, paediatric or geriatric use, the drug:surfactant ratio may range from 1:8 to 1:30, with from 1:10 to 1:27.5 being preferred.

The following examples illustrate the invention.

EXAMPLE 1

Indomethacin Capsules—Size 2

Capsules of 25 mg active ingredient per capsule were prepared using the following proportions:

| | mg per capsule |
|---|---|
| Indomethacin | 25 |
| POE(20) sorbitan monooleate (CRILLET 4) | 310 |
| Total | 335 |

The surfactant is heated to 50°-60C. and the active ingredient is then added with stirring, the latter being sufficiently vigorous to ensure that the active ingredient dissolves completely in the surfactant.

When the mixture is homogeneous and it becomes a clear solution, it is stirred for at least a further 15 minutes before filling into capsules, the temperature being maintained at 50°-60°C.

The filling of capsules requires equipment the same or similar to that used for filling Licaps of Capsugel. The capsule used in this example is the Licaps hard gelatin capsule, size 2. The capsule is filled to approximately 90% of its nominal capacity to ensure that thee is no spillage, and the cap is sealed onto the body by the Licaps sealing process. This ensures no leakage of liquid contents, or of solid contents which may melt if raised to a moderately high temperature during transport, as well as providing security against tampering.

EXAMPLES 2 TO 11

The procedure of Example 1 was repeated except that 310 mg/capsule of the surfactant indicated below was used.

In all cases the drug:surfactant weight ratio was 1:12.4.

| Example No | Surfactant |
|---|---|
| 2 | POE(20) sorbitan monoisostearate (CRILLET 6) |
| 3 | POE(40) monostearate (CRODET S24) |
| 4 | POE(24) monostearate (CRODET S40) |
| 5 | POE(40) monooleate (CRODET O40) |
| 6 | POE(20) cetostearyl ether (VOLPO CS20) |
| 7 | POE(15) cetostearyl ether (VOLPO CS15) |
| 8 | POE(20) oleyl ether (VOLPO N20) |
| 9 | POE(15) oleyl ether (VOLPO N15) |
| 10 | POE(40) hydrogenated castor oil (CREMOPHOR RH40) |
| 11 | POE(35) castor oil (ETOCAS 35) |

EXAMPLE 12

Indomethacin Capsules—Size 1

Following the procedure of Example 1, but using Size 1 capsules, capsules of 25 mg active ingredient per capsule were prepared using the following proportions:

| | mg per capsule |
|---|---|
| Indomethacin | 25 |
| POE(20) sorbitan monooleate (CRILLET 4) | 425 |
| Total | 450 |

EXAMPLES 13 TO 23

The procedure of Example 12 was repeated except that 425 mg/capsule of the surfactant indicated below was used. In all cases the drug:surfactant weight ratio was 1:17.

| Example No | Surfactant |
|---|---|
| 13 | POE(20) sorbitan monoisostearate (CRILLET 6) |
| 14 | POE(40) monostearate (CRODET S40) |
| 15 | POE(24) monostearate (CRODET S24) |
| 16 | POE(40) monooleate (CRODET O40) |
| 17 | POE(20) cetostearyl ether (VOLPO CS20) |
| 18 | POE(15) cetostearyl ether (VOLPO CS15) |
| 19 | POE(20) oleyl ether (VOLPO N20) |
| 20 | POE(15) oleyl ether (VOLPO N15) |
| 21 | POE(45) hydrogenated castor oil (CRODURET 40 or CREMOPHOR RH40) |
| 22 | POE(35) castor oil (ETOCAS 35) |
| 23 | POE(15) glyceryl monolaurate (GLYCEROX L15) |

EXAMPLE 24

Diclofenac Acid Capsules—Size 1

Capsules of 25 mg active ingredient per capsule are prepared, following generally the procedure of Example 1 but using Size 1 capsules, using the following proportions:

| | mg per capsule |
|---|---|
| Diclofenac acid | 25 |
| POE(15) cetostearyl ether (VOLPO CS15) | 425 |
| Total | 450 |

EXAMPLES 25 TO 27

The procedure of Example 24 was repeated except that 425 mg/capsule of the surfactant shown below was used.

| Example No | Surfactant |
|---|---|
| 25 | POE(20) oleyl ether (VOLPO N20) |
| 26 | POE(15) oleyl ether (VOLPO N15) |
| 27 | POE(24) monostearate (CRODET S24) |

EXAMPLE 28

Diclofenac Acid Capsules—Size 0

Capsules of 25 mg active ingredient per capsule are prepared, following generally the procedure of Example 24 but using Size 0 capsules, using the following proportions:

| | mg per capsule |
|---|---|
| Diclofenac acid | 25 |
| POE(24) monostearate (CRODET S24) | 585 |
| Total | 610 |

EXAMPLES 29 TO 35

The procedure of Example 28 was repeated except that 585 mg/capsule of the surfactant shown below was used.

| Example No | Surfactant |
|---|---|
| 29 | POE(40) monostearate (CRODET S40) |
| 30 | POE(20) sorbitan monooleate (CRILLET 4) |
| 31 | POE(20) sorbitan monoisostearate |

| Example No | Surfactant |
|---|---|
| | (CRILLET 6) |
| 32 | POE(40) hydrogenated castor oil (CRODURET 40 or CREMOPHOR RH40) |
| 33 | POE(35) castor oil (ETOCAS 35 or CREMOPHOR EL) |
| 34 | POE(15) glyceryl monolaurate (GLYCEROX L15) |
| 35 | POE(20) cetostearyl ether (VOLPO CS20) |

EXAMPLE 36

Piroxicam capsules—Size 1

Following the general procedure of Example 1, except that Size 1 capsules were used, the following capsules were made up.

| | mg per capsule |
|---|---|
| Piroxicam | 10 |
| POE(20) sorbitan monooleate (CRILLET 4) | 440 |
| Total | 450 |

EXAMPLES 37 TO 44

The procedure of Example 36 was repeated, except that 440 mg/capsule of the surfactant shown below was used.

| Example No | Surfactant |
|---|---|
| 37 | POE(20) sorbitan monoisostearate (CRILLET 6) |
| 38 | POE(20) cetostearyl ether (VOLPO CS20) |
| 39 | POE(15) cetostearyl ether (VOLPO CS15) |
| 40 | POE(20) oleyl ether (VOLPO N20) |
| 41 | POE(15) oleyl ether (VOLPO N15) |
| 42 | POE(40) hydrogenated castor oil (CREMOPHOR RH40) |
| 43 | POE(35) castor oil (ETOCAS 35) |
| 44 | POE(15) glyceryl monolaurate (GLYCEROX L15) |

EXAMPLE 45

Ketoprofen Capsules—Size 1

Capsules of 50 mg active ingredient per capsule are prepared in Size 1 gelatin capsules following the general method of Example 1 and using the following proportions:

| | mg per capsule |
|---|---|
| Ketoprofen | 50 |
| POE(20) sorbitan monooleate (CRILLET 4) | 400 |
| Total | 450 |

EXAMPLES 46 TO 51

The procedure of Example 45 was repeated, except that 400 mg/capsule of the surfactant shown below was used.

| Example No | Surfactant |
|---|---|
| 46 | POE(20) sorbitan monoisostearate (CRILLET 6) |
| 47 | POE(40) monostearate (CRODET S40) |
| 48 | POE(24) monostearate (CRODET S24) |
| 49 | POE(45) hydrogenated castor oil (CRODURET 40) |
| 50 | POE(35) castor oil (ETOCAS 35 or CREMOPHOR EL) |
| 51 | POE(24) monolaurate (CRODET L24) |

EXAMPLE 52

Ketoprofen Capsules—Size 2

The procedure of Example 45 was repeated, except that Size 2 capsules were used and the ingredients were as follows:

| | mg per capsule |
|---|---|
| Ketoprofen | 50 |
| POE(20) cetostearyl ether (VOLPO CS20) | 285 |
| Total | 335 |

EXAMPLES 53 TO 58

The procedure of Example 36 was repeated, except that 285 mg/capsule of the surfactant shown below was used:

| Example No | Surfactant |
|---|---|
| 53 | POE(15) cetostearyl ether (VOLPO CS15) |
| 54 | POE(20) oleyl ether (VOLPO N20) |
| 55 | POE(15) oleyl ether (VOLPO N15) |
| 56 | POE(40) glyceryl monolaurate (GLYCEROX L40) |
| 57 | POE(40) hydrogenated castor oil (CRODURET 40) |
| 58 | POE(35) castor oil (ETOCAS 35) |

It should be noted that if Size 2 capsules formulate satisfactorily then it follows that Size 1 will too.

EXAMPLE 59

Naproxen Capsules—Size 1

Capsules of 25 mg active ingredient per capsule are prepared in Size 1 gelatin capsules following the general method of Example 1 and using the following proportions:

| | mg per capsule |
|---|---|
| Naproxen | 25 |
| POE(15) cetostearyl ether (VOLPO CS15) | 425 |
| Total | 450 |

EXAMPLES 60 TO 62

The procedure of Example 59 was repeated, except that 425 mg/capsule of the surfactant shown below was used.

| 60 | POE(20) cetostearyl ether (VOLPO CS20) |
|---|---|
| 61 | POE(15) oleyl ether (VOLPO N15) |
| 62 | POE(20) oleyl ether (VOLPO N20) |

EXAMPLE 63

Flufenamic Acid Capsules—Size 0

Capsules of 50 mg active ingredient per capsule are prepared in Size 0 gelatin capsules following the general method of Example 1 and using the following proportions:

|  | mg per capsule |
|---|---|
| Flufenamic Acid | 50 |
| POE(24) monolaurate (CRODET L24) | 560 |
| Total | 610 |

EXAMPLES 64 TO 73

The procedure of Example 63 was repeated, except that 560 mg/capsule of the surfactant shown below was used:

| 64 | POE(24) monostearate (CRODET S24) |
|---|---|
| 65 | POE(40) monostearate (CRODET S40) |
| 66 | POE(20) sorbitan monooleate (CRILLET 4) |
| 67 | POE(20) sorbitan monoisostearate (CRILLET 6) |
| 68 | POE(4) hydrogenated castor oil (CREMOPHOR RH40) |
| 69 | POE(15) glyceryl monolaurate (GLYCEROX L15) |
| 70 | POE(15) cetostearyl ether (VOLPO CS15) |
| 71 | POE(20) cetostearyl ether (VOLPO CS20) |
| 72 | POE(15) oleylether (VOLPO N15) |
| 73 | POE(20) oleylether (VOLPO N20) |

EXAMPLE 74

Flufenamic Acid Capsules—Size 1

Capsules of 50 mg active ingredient per capsule are prepared in Size 1 gelatin capsules following the general method of Example 1 and using the following proportions:

|  | mg per capsule |
|---|---|
| Flufenamic Acid | 50 |
| POE(40) hydrogenated castor oil (CREMOPHOR RH40) | 400 |
| Total | 450 |

EXAMPLES 75 TO 77

The procedure of Example 74 was repeated, except that 400 mg/capsule of the surfactant shown below was used:

| 75 | POE(15) cetostearyl ether (VOLPO CS15) |
|---|---|
| 76 | POE(20) cetostearyl ether (VOLPO CS20) |
| 77 | POE(15) oleyl ether (VOLPO N15) |

EXAMPLE 78

Ibuprofen Capsules—Size 0

Capsules of 50 mg active ingredient per capsule are prepared in Size 0 gelatin capsules following the general method of Example 1 and using the following proportions:

|  | mg per capsule |
|---|---|
| Ibuprofen | 50 |
| POE(24) monolaurate (CRODET L24) | 560 |
| Total | 610 |

EXAMPLES 79 TO 87

The procedure of Example 78 was repeated, except that 560 mg/capsule of the surfactant shown below was used:

| 79 | POE(24) monostearate (CRODET S24) |
|---|---|
| 80 | POE(20) sorbitan monooleate (CRILLET 4) |
| 81 | POE(20) sorbitan monoisostearate (CRILLET 6) |
| 82 | POE(40) hydrogenated castor oil (CREMOPHOR RH40) |
| 83 | POE(15) glyceryl monolaurate (GLYCEROX L15) |
| 84 | POE(15) cetostearyl ether (VOLPO CS15) |
| 85 | POE(20) cetostearyl ether (VOLPO CS20) |
| 86 | POE(15) oleyl ether (VOLPO N15) |
| 87 | POE(15) oleyl ether (VOLPO N20) |

EXAMPLE 88

Ibuprofen Capsules—Size 1

Capsules of 50 mg active ingredient per capsule are prepared in Size 1 gelatin capsules following the general method of Example 1 and using the following proportions:

|  | mg per capsule |
|---|---|
| Ibuprofen | 50 |
| POE(24) monolaurate | 400 |
| Total | 450 |

EXAMPLES 89 TO 94

The procedure of Example 88 was repeated, except that 400 mg/capsule of the surfactant shown below was used:

| 89 | POE(20) sorbitan monoisostearate (CRILLET 6) |
|---|---|
| 90 | POE(40) hydrogenated castor oil (CREMOPHOR RH40) |
| 91 | POE(15) cetostearyl ether (VOLPO CS15) |
| 92 | POE(20) cetostearyl ether (VOLPO CS20) |
| 93 | POE(15) oleyl ether (VOLPO N15) |
| 94 | POE(20) oleyl ether (VOLPO N20) |

EXAMPLE 95

Indomethacin Solution

A solution of indomethacin for paediatric or geriatric use may be made according to the following proportions of principal ingredients, the potency being 25 mg per 5 ml, and the dispensed quantity 200 ml:

|  | Quantity per 200 ml |
|---|---|
| Indomethacin | 1.00 g |
| Surfactant (POE(20) sorbitan monooleate) | 20.0 g |
| Preservative (potassium sorbate) | 0.40 g |
| Sweetener (sodium saccharin) | qs |
| Citric acid | qs |
| Flavouring | qs |
| Water, purified | to 200 ml |

Approximately half the required water is placed in a suitable container, together with the potassium sorbate (or other suitable preservative), and the sodium saccharin (or other potent sweetener). The solution is stirred and heated continuously to 50°-55°0 C. This forms the aqueous phase.

The surfactant (in this example POE (20) sorbitan monooleate e.g. CRILLET 4 or TWEEN 80) is heated to 50°-55° C. with continuous stirring in a separate suitable container. The indomethacin is then added and stirring is continued until 15 minutes after all the active ingredient has dissolved, the temperature being maintained at 50°-55° C. This comprises the non-aqueous phase.

The aqueous phase is then added to the non-aqueous phase with continuous stirring. The addition should be fairly rapid. A clear, slightly yellow solution is formed which is then stirred until cool, no further heating being applied after the start of the addition of the aqueous phase to the non-aqueous phase. The solution is then adjusted to give the correct potency by addition of purified water.

pH adjustment is by addition of citric acid until a pH of 3.0–3.5 is reached, the solution being continuously stirred and the citric acid being allowed to completely dissolve before a pH measurement is made. Flavouring is added according to requirements. The solution is then ready for bottling.

EXAMPLES 96 AND 97

Indomethacin solutions are prepared as in Example 95, except that 20 g of the following surfactants were used:

| 96 | POE(20) sorbitan monoisostearate (CRILLET 6) |
| 97 | POE(35) castor oil (CREMOPHOR EL) |

EXAMPLE 98

Diclofenac Solution

A solution of diclofenac for paediatric or geriatric use may be made, following the general procedure of Example 95, according to the following proportions of principal ingredients, the potency being 25 mg per 5 ml, and the dispensed quantity 200 ml:

|  | Quantity per 200 ml |
|---|---|
| Diclofenac Acid | 1.00 g |
| POE(40) hydrogenated castor oil (CREMOPHOR RH40) | 27.5 g |
| Preservative (potassium sorbate) | 0.40 g |
| Sweetener (sodium saccharin) | qs |
| Citric Acid | qs |
| Flavouring | qs |
| Water, purified | to 200 ml |

EXAMPLE 99

A diclofenac solution is prepared as in Example 98, except that 27.5 g POE(35) castor oil (CREMOPHOR EL) is used.

EXAMPLE 100

Ketoprofen Solution

A solution of ketoprofen for paediatric or geriatric use may be made following the general procedure of Example 95, according to the following proportions of principal ingredients, the potency being 25 mg per 5 ml, and the dispensed quantity 200 ml:

|  | Quantity per 200 ml |
|---|---|
| Ketoprofen | 1.00 g |
| Surfactant POE (20) sorbitan monoisostearate (CRILLET 6) | 10.0 g |
| Preservative (potassium sorbate) | 0.40 g |
| Sweetener (sodium saccharin) | qs |
| Citric acid | qs |
| Flavouring | qs |
| Water, purified | to 200 ml |

EXAMPLE 101–103

A ketoprofen solution is prepared as in Example 100, except that 10 g of the following surfactants were used:

| 101 | POE(40) monostearate (CRODET S40) |
| 102 | POE(20) sorbitan monooleate (CRILLET 4 or TWEEN 80) |
| 103 | POE(40) hydrogenated castor oil (CREMOPHOR RH40) |

EXAMPLE 104

Flurbiprofen Capsules—Size 1

Capsules of 50 mg active ingredient per capsule were prepared in Size 1 gelatin capsules following generally the procedure of Example 1 and using the following proportions:

|  | mg per capsule |
|---|---|
| Flurbiprofen | 50 |
| POE(40) hydrogenated castor oil (CRODURET 40) | 400 |
| Total: | 450 |

EXAMPLES 105 TO 109

The procedure of Example 104 was repeated, except that 400 mg/capsule of the surfactant shown below was used.

| Example No. | Surfactant |
|---|---|
| 105 | POE(35) castor oil (ETOCAS 35) |
| 106 | POE(20) cetostearyl ether (VOLPO CS20) |
| 107 | POE(15) cetostearyl ether (VOLPO CS15) |
| 108 | POE(20) oleyl ether (VOLPO N20) |
| 109 | POE(15) oleyl ether (VOLPO N15) |

EXAMPLE 110

Fluribprofen Capsules—Size 0

Following the procedure of Example 104, but using Size 0 capsules, capsules of 50 mg of active ingredient per capsule were prepared using the following proportions:

|  | mg per capsule |
|---|---|
| Flurbiprofen | 50 |
| POE(20) sorbitan monooleate (CRILLET 4) | 560 |
| Total: | 610 |

EXAMPLE 111 TO 121

The procedure of Example 110 was repeated, except that 560 mg/capsule of the surfactant shown below was used.

| Example No. | Surfactant |
|---|---|
| 111 | POE(40) hydrogenated castor oil (CREMOPHOR RH40 or CRODURET 40) |
| 112 | POE(35) castor oil (ETOCAS 35 or CREMOPHOR EL) |
| 113 | POE(24) monolaurate (CRODET L24) |
| 114 | POE(24) monostearate (CRODET S24) |
| 115 | POE(20) sorbitan monoisostearate (CRILLET 6) |
| 116 | POE(60) hydrogenated castor oil (CREMOPHOR RH60) |
| 117 | POE(15) glyceryl monolaurate (GLYCEROX L15) |
| 118 | POE(15) cetostearyl ether (VOLPO CS15) |
| 119 | POE(20) cetostearyl ether (VOLPO CS20) |
| 120 | POE(15) oleyl ether (VOLPO N15) |
| 121 | POE(20) oleyl ether (VOLPO N20) |

EXAMPLE 122

Slow Release Indomethacin Capsule

Capsules of 75 mg active ingredient per capsule were prepared using the following proportions:

|  | mg per capsule |
|---|---|
| Indomethacin | 75 |
| GELUCIRE 46/07 | 214 |
| POE(24) monostearate [CRODET S24] | 321 |
| Total: | 610 |

GELUCIRE 46/07 (by Gattefosse) is a mixture of glycerol and PEG fatty acid esters, with melting point of 43°–49° C., HLB of 7, and oral toxicity of LDO>20 g/kg.

The GELUCIRE 46/07 and the POE(24) monostearate were heated, melted and mixed together to 55°–60° C. and the indomethacin was then added with stirring, the latter being sufficiently vigorous to ensure that the active ingredient was dissolved completely in the mix. The mixture was then filled into hard gelatin capsules, Size 0.

EXAMPLE 123

The proceudre of Example 122 was repeated except that the following ingredients were used in the formulation:

|  | mg per capsule |
|---|---|
| Indomethacin | 75 |
| GELUCIRE 50/02 | 214 |
| POE(24) monostearate [CRODET S24] | 321 |
| Total: | 610 |

GELUCIRE 50/02 (by Gattefosse) is a mixture of glycerol and PEG fatty acid esters, with melting point of 48°–52° C., HLB of 2, and oral toxicity of LD50>18 g/kg.

EXAMPLE 124

The procedure of Example 122 was repeated except that the following ingredients were used in this formulation:

|  | mg per capsule |
|---|---|
| Indomethacin | 75 |
| GELUCIRE 53/10 | 161 |
| POE(24) monostearate [CRODET S24] | 374 |
| Total: | 610 |

GELUCIRE 53/10 (by Gattefosse) is a mixture of glycerol and fatty acid esters, with melting point of 51°–56° C., HLB of 10, and oral toxicity of LDO>20 g/kg.

EXAMPLE 125

The procedure of Example 122 was repeated except that the following ingredients were used in the formulation:

|  | mg per capsule |
|---|---|
| Indomethacin | 75 |
| GELUCIRE 53/10 | 214 |
| POE(24) monostearate [CRODET S24] | 321 |
| Total: | 610 |

EXAMPLE 126

The procedure of Example 122 was repeated except that the following ingredients were used in the formulation:

|  | mg per capsule |
|---|---|
| Indomethacin | 75 |
| GELUCIRE 53/10 | 267 |
| POE(24) monostearate [CRODET S24] | 268 |
| Total: | 610 |

EXAMPLE 127

The procedure of Example 122 was repeated except that the following ingredients were used in the formulation:

|  | mg per capsule |
|---|---|
| Indomethacin | 75 |
| GELUCIRE 53/10 | 321 |
| POE(24) monostearate [CRODET S24] | 214 |
| Total: | 610 |

EXAMPLE 128

Capsules from Examples 122 to 127 were assessed for their dissolution rate using U.S. Pat. Apparatus No. 2 (USPXXI) with a paddle speed of 100 rpm, the dissolution medium being 0.2 M phosphate buffer pH 7.2 maintained at 37° C.

Aliquots were taken at hourly intervals and the amount of indomethacin dissolved was determined by UV spectrophotometric absorption at 318 nm. The results which are the average of three capsules are as follows:

| Percentage of Indomethacin dissolved | | | | | |
|---|---|---|---|---|---|
| Time (h) | Example 122 | Example 123 | Example 124 | Example 125 | Example 126 | Example 127 |
| 1 | 36.0 | 26.1 | 31.2 | 26.4 | 25.9 | 19.0 |
| 2 | 59.3 | 42.6 | 44.2 | 37.7 | 37.4 | 27.5 |
| 3 | 78.0 | 54.1 | 55.2 | 46.8 | 44.9 | 33.7 |
| 4 | 84.5 | 64.0 | 66.0 | 55.1 | 51.5 | 39.0 |
| 5 | 90.2 | 71.9 | 75.7 | 63.1 | 57.5 | 44.1 |
| 6 | 94.0 | 78.6 | 85.1 | 70.1 | 63.4 | 48.7 |
| 7 | 97.0 | 84.0 | 91.4 | 76.4 | 69.6 | 52.9 |
| 8 | 98.7 | 88.6 | 95.7 | 81.9 | 74.7 | 57.2 |
| 9 | 99.7 | 90.6 | 97.7 | 86.0 | 79.2 | 61.8 |
| 10 | 100.0 | 92.3 | 98.9 | 89.8 | 83.2 | 66.2 |
| 11 | 100.0 | 92.8 | 98.8 | 92.4 | 86.3 | 70.2 |
| 12 | 100.0 | 92.8 | 98.4 | 93.8 | 88.3 | 73.6 |

What is claimed is:

1. A method for the treatment of prophylaxis of inflammatory arthropathy, the method comprising the steps of:
providing a non-aqueous formulation of a non-steroidal anti-inflammatory drug and a surfactant, the formulation forming micelles containing the drug on oral administration; and
orally administering said formulation to a patient to be treated.

2. The method of claim 1, further comprising selecting said non-steroidal anti-inflammatory drug from the class consisting of diclofenac, flufenamic acid, flurbiprofen, ibuprofen, indomethacin, ketoprofen, naproxen, phenylbutazone, piroxicam and sulindac and mixtures thereof.

3. The method of claim 1, further comprising selecting a nonionic surfactant as said surfactant.

4. The method of claim 3, further comprising selecting from a polyoxyethylated surfactant as said nonionic surfactant.

5. The method of claim 4 further comprising selecting said surfactant from the class consisting of polyoxyethylated glycol monoethers, polyoxyethylated fatty acids, polyoxyethylated sorbitan fatty esters and polyoxyethylated castor oils.

6. The method of claim 4, further comprising selecting said nonionic surfactant from the class consisting of sorbitan fatty acid esters, poloxamers, polyethylene glycol fatty acid esters and polyethyoxylated glyceryl fatty acid esters and mixtures thereof.

7. The method of claim 1, further comprising selecting a surfactant having an HLB of 10 or above.

8. The method of claim 1, further comprising selecting a surfactant having an HLB of 12 or above.

9. The method of claim 1, further comprising providing said formulation in the form of a capsule.

10. The method of claim 1, further comprising providing said formulation in the form of a liquid.

11. The method of claim 1, further comprising providing said drug and surfactant in a weight ratio in the formulation in a range of from 1:5.7 to 1:50.

12. The method of claim 1, further comprising providing said drug and surfactant in a weight ratio in the formulation is in a range from 1:6 to 1:25.

13. The method of claim 1, further comprising providing said drug and surfactant in a weight ratio in the formulation is in a range of from 1:6 to 1:20.

14. The method of claim 1, further comprising providing said drug and surfactant in a weight ratio in the formulation is in a range of from 1:8 to 1:30.

15. The method of claim 1, further comprising providing said drug and surfactant in a weight ratio in the formulation is in a range of from 1:10 to 1:27.5.

* * * * *

UNITED STATES PATENT AND TRADEMARK OFFICE
CERTIFICATE OF CORRECTION

PATENT NO. : 4,944,949

DATED : July 31, 1990

INVENTOR(S) : Michael J. Story, et al.

It is certified that error appears in the above-identified patent and that said Letters Patent is hereby corrected as shown below:

Col. 7, line 13, "registers" should be --registering--.

Col. 19, line 5, "50° - 55° OC" should be --50° - 55° C--.

Col. 23, line 20, "of" (1st occurence) should be --or--.

Signed and Sealed this

Seventh Day of January, 1992

Attest:

HARRY F. MANBECK, JR.

*Attesting Officer*      *Commissioner of Patents and Trademarks*